(12) United States Patent
Seeboth et al.

(10) Patent No.: US 9,096,557 B2
(45) Date of Patent: *Aug. 4, 2015

(54) THIADIAZOLE WHICH CAN BE USED AS A VULCANIZATION ACCELERATOR AND METHOD FOR OBTAINING SAME

(75) Inventors: Nicolas Seeboth, Clermont-Ferrand (FR); Sergey Ivanov, Orekhovo-Zouevo (RU)

(73) Assignees: COMPAGNIE GENERALE DES ETABLISSEMENTS MICHELIN, Clermont-Ferrand (FR); Michelin Recherche et Technique S.A., Granges-Paccot (CH)

( * ) Notice: Subject to any disclaimer, the term of this patent is extended or adjusted under 35 U.S.C. 154(b) by 328 days.

This patent is subject to a terminal disclaimer.

(21) Appl. No.: 13/501,096

(22) PCT Filed: Oct. 8, 2010

(86) PCT No.: PCT/EP2010/065070
§ 371 (c)(1),
(2), (4) Date: Sep. 21, 2012

(87) PCT Pub. No.: WO2011/042523
PCT Pub. Date: Apr. 14, 2011

(65) Prior Publication Data
US 2013/0046099 A1   Feb. 21, 2013

(30) Foreign Application Priority Data

Oct. 8, 2009  (FR) ..................... 09 57038

(51) Int. Cl.
*C07D 285/125* (2006.01)
*C08K 5/46* (2006.01)
*C08L 21/00* (2006.01)
*C08L 9/06* (2006.01)
*C08K 5/00* (2006.01)

(52) U.S. Cl.
CPC .......... *C07D 285/125* (2013.01); *C08K 5/0025* (2013.01); *C08K 5/46* (2013.01)

(58) Field of Classification Search
CPC ...... C07D 285/125; C08K 5/46; C08K 5/0025
See application file for complete search history.

(56) References Cited

U.S. PATENT DOCUMENTS

| 2,666,043 | A | * | 1/1954 | Carr et al. ................. 525/332.7 |
| 2,899,439 | A |   | 8/1959 | Korman |
| 2,983,716 | A |   | 5/1961 | Fields |

FOREIGN PATENT DOCUMENTS

| DE | 2151895 | 4/1973 |
| FR | 2320297 | 3/1977 |
| JP | 04157458 A * | 5/1992 |

OTHER PUBLICATIONS

English language abstract of JP 04157458 A by Nagaoka et al., 1992, Chemical Abstracts Service.*
Ex parte Cao, Decision rendered by the Board of Patent Appeals and Interferences in U.S. Appl. No. 10/696,862 on Sep. 21, 2011.*

* cited by examiner

*Primary Examiner* — Matthew Coughlin
(74) *Attorney, Agent, or Firm* — Cozen O'Connor

(57) ABSTRACT

A thiadiazole of formula (I):

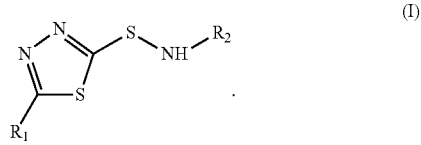

10 Claims, No Drawings

THIADIAZOLE WHICH CAN BE USED AS A VULCANIZATION ACCELERATOR AND METHOD FOR OBTAINING SAME

RELATED APPLICATIONS

This application is a U.S. National Phase Application under 35 USC 371 of International Application No. PCT/EP2010/065070, filed on Oct. 8, 2010.

This patent application claims the priority of the French patent application no. 09/57038 filed Oct. 8, 2009.

FIELD OF THE INVENTION

The present invention relates to a specific thiadiazole, to its process of preparation and to its use as vulcanization accelerator.

BACKGROUND OF THE INVENTION

The vulcanization of diene elastomers by sulphur is widely used in the rubber industry, in particular the tire industry. Use is made, in order to vulcanize diene elastomers, of a relatively complex vulcanization system comprising, in addition to the sulphur, a primary vulcanization accelerator, such as sulphenamides comprising a benzothiazole ring system, and also various secondary vulcanization accelerators or vulcanization activators, very particularly zinc derivatives, such as zinc oxide (ZnO) alone or used with fatty acids.

These vulcanization accelerators have to induce sufficient crosslinking while retaining an acceptable compromise between the various rheometric properties.

SUMMARY OF THE INVENTION

The inventors have discovered a novel thiadiazole compound which can be used as vulcanization accelerator for rubber compositions. In particular, this novel compound makes it possible, in a use for rubber compositions for tyres, to obtain a compromise in rheometric properties similar to that obtained with vulcanization accelerators conventionally used.

One aspect of the invention is directed to a thiadiazole of formula (I):

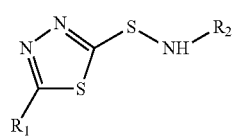

(I)

where $R_1$ represents H or a $C_1$-$C_{25}$ hydrocarbon group chosen from linear, branched or cyclic alkyl groups and aryl groups which are optionally interrupted by one or more heteroatoms, $R_2$ represents:
  a linear or branched $C_1$-$C_{25}$ alkyl group which is optionally interrupted by one or more heteroatoms and which is optionally substituted by one or more cyclic $C_3$-$C_{10}$ alkyl or $C_6$-$C_{12}$ aryl groups, or
  a cyclic $C_3$-$C_{10}$ alkyl group which is optionally interrupted by one or more heteroatoms and which is optionally substituted by one or more linear, branched or cyclic $C_1$-$C_{25}$ alkyl or $C_6$-$C_{12}$ aryl groups which are optionally interrupted by one or more heteroatoms.

A further aspect of the invention is directed to a process for the preparation of a thiadiazole as defined above, comprising the following stages:
  the starting compound is compound (A) of following formula:

(A)

where $R_1$ is as defined above,
  compound (A) is reacted with a compound of formula $R_2NH_2$, where $R_2$ is as defined above, in the presence of an organic or inorganic base, then
  an oxidizing composition comprising at least one oxidizing agent is added to the reaction medium, in order to obtain the thiadiazole of formula (I).

A final aspect of the invention is directed to the use, as vulcanization accelerator, of a thiadiazole as defined above.

DETAILED DISCUSSION

The invention and its advantages will be easily understood in the light of the description and implementational examples which follow.

I. Measurements and Tests Used

The rubber compositions in which the thiadiazole vulcanization accelerators are tested are characterized, before and after curing, as indicated below.

Rheometry

The measurements are carried out at 150° C. with an oscillating disc rheometer, according to Standard DIN 53529—part 3 (June 1983). The change in the rheometric torque, ΔTorque, as a function of time describes the change in the stiffening of the composition as a result of the vulcanization reaction. The measurements are processed according to Standard DIN 53529—part 2 (March 1983): $t_0$ is the induction period, that is to say the time necessary for the start of the vulcanization reaction; $t_\alpha$ (for example $t_{99}$) is the time necessary to achieve a conversion of α%, that is to say α% (for example 99%) of the difference between the minimum and maximum torques. The conversion rate constant, denoted K (expressed in $min^{-1}$), which is first order, calculated between 30% and 80% conversion, which makes it possible to assess the vulcanization kinetics, is also measured.

II. Conditions for the Implementation of the Invention

II-1. Thiadiazole of the Invention

As explained above, the first subject-matter of the invention is a thiadiazole of following formula (I):

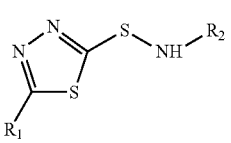

(I)

where
$R_1$ represents H or a $C_1$-$C_{25}$ hydrocarbon group chosen from linear, branched or cyclic alkyl groups and aryl groups which are optionally interrupted by one or more heteroatoms, $R_2$ represents:
  a linear or branched $C_1$-$C_{25}$ alkyl group which is optionally interrupted by one or more heteroatoms and which is optionally substituted by one or more cyclic $C_2$-$C_{10}$ alkyl or $C_6$-$C_{12}$ aryl groups, or
  a cyclic $C_3$-$C_{10}$ alkyl group which is optionally interrupted by one or more heteroatoms and which is optionally substituted by one or more linear, branched or cyclic $C_1$-$C_{25}$ alkyl or $C_6$-$C_{12}$ aryl groups which are optionally interrupted by one or more heteroatoms.

Cyclic alkyl group is understood to mean an alkyl group composed of one or more rings.

The heteroatom or heteroatoms can be a nitrogen, sulphur or oxygen atom.

Preferably, the thiadiazole compound of formula (I) is such that:
  $R_1$ represents H or a $C_1$-$C_{25}$ hydrocarbon group chosen from linear, branched or cyclic alkyl groups and aryl groups which are optionally interrupted by one or more heteroatoms,
  $R_2$ represents:
  a linear $C_2$-$C_{25}$ or branched $C_3$ or $C_5$-$C_{25}$ alkyl group which is optionally interrupted by one or more heteroatoms and which is optionally substituted by one or more cyclic $C_3$-$C_{10}$ alkyl or $C_6$-$C_{12}$ aryl groups, or
  a cyclic $C_3$-$C_{10}$ alkyl group which is optionally interrupted by one or more heteroatoms and which is optionally substituted by one or more linear, branched or cyclic $C_1$-$C_{26}$ alkyl or $C_6$-$C_{12}$ aryl groups which are optionally interrupted by one or more heteroatoms.

According to a first embodiment, $R_1$ represents a methyl group.

According to a second embodiment, $R_1$ represents H.

Advantageously, $R_2$ represents a cyclic $C_3$-$C_{10}$ alkyl group. In particular, $R_2$ can represent a cyclohexyl group.

Hence a preferred compound of formula (I) is that in which $R_1$ represents H and $R_2$ represents a cyclohexyl. In this case, the thiadiazole compound of formula (I) is N-cyclohexyl-S-(1,3,4-thiadiazol-2-yl)thiohydroxyl-amine.

Another preferred compound of formula (I) is that in which $R_1$ represents a methyl and $R_2$ represents a cyclohexyl. In this case, the thiadiazole compound of formula (I) is N-cyclohexyl-S-(5-methyl-1,3,4-thiadiazol-2-yl)thiohydroxy-lamine.

II-2. Synthetic Process

According to the invention, the process for producing a thiadiazole of formula (I) as defined above comprises the following stages:
  the starting compound is compound (A) of the following formula:

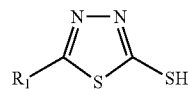

(A)

where $R_1$ is as defined above,
  compound (A) is reacted with a compound of formula $R_2NH_2$, or $R_2$ is as defined above, in the presence of an organic or inorganic base, then
  an oxidizing composition comprising at least one oxidizing agent is added to the reaction medium, in order to obtain the thiadiazole of formula (I).

According to a first embodiment, $R_1$ represents hydrogen.

According to a second embodiment, $R_1$ represents a methyl group.

Preferably, $R_2$ represents a cyclohexyl group.

When compound (A) is reacted in the presence of a base, the latter can, for example, be an aqueous sodium hydroxide solution.

As explained above, the process according to the invention comprises a stage of addition of an oxidizing composition. The oxidizing agent can be chosen from conventional oxidizing agents, such as bromine, chlorine or iodine, hypobromic acid, hypochloric acid or hypoiodic acid, or else the alkali metal salts of the above acids. Generally, an aqueous sodium hypochlorite solution is preferred.

II-3. Use as Vulcanization Accelerator

As indicated above, the thiadiazole compound of the invention has an advantageous and industrial application as vulcanization accelerator. It can thus be used in a rubber composition for the manufacture of tires, based on one or more diene elastomers, on one or more reinforcing fillers and on a vulcanization system.

For such a use, the diene elastomer or elastomers is/are preferably chosen from the group of highly unsaturated diene elastomers consisting of polybutadienes (abbreviated to "BR"), synthetic polyisoprenes (IR), natural rubber (NR), butadiene copolymers, isoprene copolymers and the mixtures of these elastomers. Such copolymers are more preferably chosen from the group consisting of butadiene/styrene copolymers (SBR), isoprene/butadiene copolymers (SIR), isoprene/styrene copolymers (SIR) and isoprene/butadiene/styrene (SBIR) copolymers.

Furthermore, use may be made of any type of reinforcing filler known for its abilities to reinforce a rubber composition which can be used in the manufacture of tires, for example an organic filler, such as carbon black, a reinforcing inorganic filler, such as silica, or a blend of these two types of filler, in particular a blend of carbon black and silica.

The term "reinforcing inorganic filler" should be understood in the present patent application, by definition, as meaning any inorganic or mineral filler, whatever its colour or its origin (natural or synthetic), also known as "white filler", "clear filler", indeed even "non-black filler", in contrast to carbon black, capable of reinforcing by itself alone, without means other than an intermediate coupling agent, a rubber composition intended for the manufacture of tires, in other words capable of replacing, in its reinforcing role, a conventional tire-grade carbon black; such a filler is generally characterized, in a known way, by the presence of hydroxyl (—OH) groups at its surface.

Suitable in particular as reinforcing inorganic fillers are mineral fillers of siliceous type, in particular silica ($SiO_2$).

The vulcanization system proper is based on sulphur (or on a sulphur-donating agent) and on a primary vulcanization accelerator. Additional to this base vulcanization system are various known secondary vulcanization accelerators or vulcanization activators, such as zinc oxide, stearic acid or equivalent compounds, or guanidine derivatives (in particular diphenylguanidine).

The primary vulcanization accelerator must allow rubber compositions to crosslink within industrially acceptable times while retaining a minimum safety period ("scorch time") during which the compositions can be shaped without risk of premature vulcanization ("scorching").

The thiadiazole compound according to the invention can thus be used as vulcanization accelerator. It replaces, in all or in part, the normal sulphonamide compounds.

III. Examples of the Implementation of the Invention

In the following examples, the synthesis of two specific thiadiazole compounds according to the invention is presented, and then the invention is implemented with N-cyclohexyl-S-(1,3,4-thiadiazol-2-yl)thiohydroxylamine (compound B).

III-1. Synthesis of the compound N-cyclohexyl-S-(1,3,4-thiadiazol-2-yl)thiohydroxylamine (compound B)

Compound B has the formula:

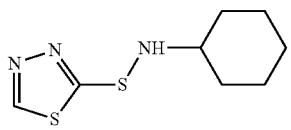 [SMILES: c1nnc(SNC2CCCCC2)s1]

This compound is prepared from 1,3,4-thiadiazole-2-thiol and cyclohexylamine according to the following synthetic scheme:

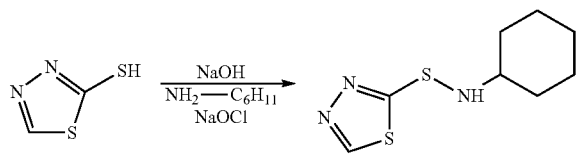

1,3,4-Thiadiazole-2-thiol is commercially available (CAS number [18686-82-3]). It can be obtained from carbon disulphide and hydrazine hydrate according to procedures described in the following documents:
1. CH 563 380 (1971)
2. FR 71 47 384 (1972)

The reaction scheme for the preparation of 1,3,4-thiadiazole-2-thiol is as follows:

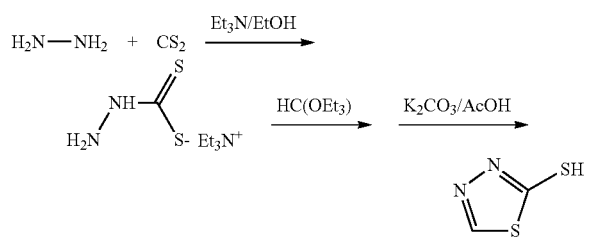

Cyclohexylamine (77.35 g, 0.78 mol) is added to a solution of 1,3,4-thiadiazole-2-thiol (18.44 g, 0.16 mol) and sodium hydroxide (14.04 g, 0.35 mol) in water (900 ml). The mixture is cooled to 0-5° C. and then the aqueous NaOCl solution (4% active chlorine) (343 ml) is added dropwise over 15 minutes. The temperature of the reaction medium is maintained between 0 and +5° C. The reaction medium is subsequently stirred at a temperature of between 0 and 5° C. for from one to one and a half hours.

Petroleum ether (100 ml) is added and the reaction mixture is subsequently stirred at a temperature of between 0 and −4° C. for from 15 to 30 minutes. The precipitate is filtered off, washed with water (200 ml) and petroleum ether (50 ml) and then dried for from 2 to 3 hours under reduced pressure and for 12 hours at ambient temperature.

A white solid (11.0 g, 0.05 mol) with a melting point of 81-83° C. is obtained.

The molar purity is greater than 96% (H NMR).

The product is completely characterized by NMR. The chemical shifts obtained by $^1$H NMR in $d_6$-acetone are given in the table below. Calibration is carried out with regard to acetone (1.98 ppm in $^1$H).

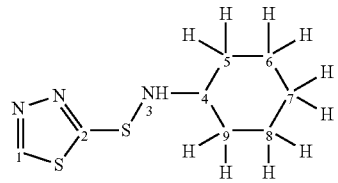

| | 1 | 2 | 3 | 4 | 5 | 6 | 7 | 8 | 9 |
|---|---|---|---|---|---|---|---|---|---|
| δ $^1$H (ppm) | 9.21 | — | 4.72 | 2.81 | 1.98 1.19 | 1.67 1.25 | 1.52 1.14 | 1.67 1.25 | 1.98 1.19 |

III-2. Synthesis of the compound N-cyclohexyl-S-(5-methyl-1,3,4-thiadiazol-2-yl)thiohydroxylamine N-Cyclohexyl-S-(5-methyl-1,3,4-thiadiazol-2-yl)thiohydroxylamine has a formula:

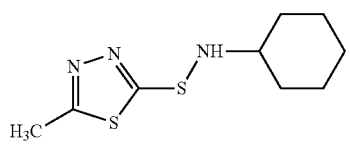

This compound is prepared from 5-methyl-1,3,4-thiadiazole-2-thiol and cyclohexylamine according to the following synthetic scheme:

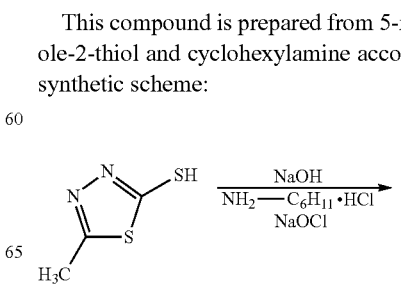

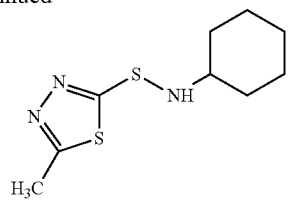

5-Methyl-1,3,4-thiadiazole-2-thiol is commercially available (CAS number [29490-19-5]). It can be obtained from carbon disulphide and acetylhydrazine according to procedures described in the following documents:
1. CH 563 380 (1971)
2. FR 71 473 84 (1972)

The reaction scheme for the preparation of 5-methyl-1,3,4-thiadiazole-2-thiol is as follows:

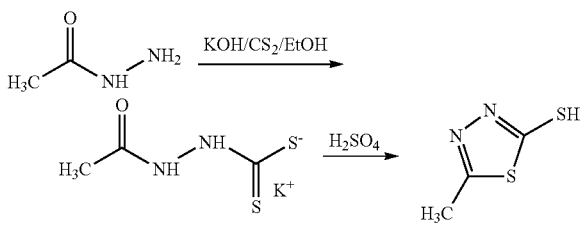

Cyclohexylamine hydrochloride (192.30 g, 1.42 mol) is added to a solution of 5-methyl-1,3,4-thiadiazole-2-thiol (37.50 g, 0.28 mol) and sodium hydroxide (85.20 g, 2.13 mol) in water (1 l). The mixture is cooled to a temperature of between 0 and −5° C. and then the aqueous NaOCl solution (4% active chlorine) is added dropwise over from 15 to 30 minutes. The temperature of the reaction medium is maintained between 0 and +5° C. The reaction medium is subsequently stirred at a temperature of between 0 and +5° C. for from 1 h 30 to 2 hours.

Petroleum ether (100 ml) is added and the reaction medium is subsequently stirred at a temperature of between 0 and −4° C. for from 1 h 30 to 2 hours. The precipitate is filtered off, washed with water (200 ml) and petroleum ether (50 ml) and finally dried for from 2 to 3 hours under reduced pressure and for 12 hours at ambient temperature.

A white solid (23.27 g, 0.10 mol) with a melting point of 94-96° C. is obtained.

The molar purity is greater than 97% ($^1$H NMR).

The product is completely characterized by NMR. The chemical shifts obtained by $^1$H NMR in $d_6$-acetone are given in the table below. Calibration is carried out with regard to acetone (1.98 ppm in $^1$H).

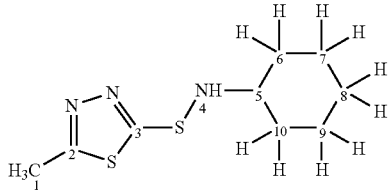

III-3. Use as Vulcanization Accelerator—Preparation of the Compositions

The procedure for the following tests is as follows: the diene elastomer or elastomers, the reinforcing filler or fillers and the optional coupling agent, followed, after kneading for from 1 to 2 minutes, by the various other ingredients, with the exception of the vulcanization system, are introduced into an internal mixer, 70% filled and having a starting vessel temperature of approximately 90° C. Thermomechanical working (nonproductive phase) is then carried out in one stage (total duration of the kneading equal to approximately 5 min), until a maximum "dropping" temperature of approximately 165° C. is reached. The mixture thus obtained is recovered and cooled, and then the covering agent (when there is one present) and the vulcanization system (sulphur and thiadiazole compound (or "CBS" for the comparative example)) are added on an external mixer (homofinisher) at 70° C., everything being mixed (productive phase) for approximately from 5 to 6 min.

The compositions thus obtained are subsequently calendered, either in the form of plaques (thickness of to 3 mm) or thin sheets of rubber, for the measurement of their physical or mechanical properties, or in the form of profiled elements which can be used directly, after cutting out and/or assembling to the desired dimensions, for example as semifinished products for tires, in particular as tire treads.

III-4. Characterization Tests—Results

The object of this example is to compare the rheometric properties of a rubber composition, which can be used in the manufacture of a tire tread, comprising N-cyclohexyl-S-(1,3,4-thiadiazol-2-yl)thiohydroxylamine (compound B) as primary vulcanization accelerator (composition 2), with the properties of a rubber composition comprising N-cyclohexyl-2-benzothiazolesulphenamide ("CBS") (composition 1).

The formulations of the compositions are given in Table 1. The amounts are expressed as parts per 100 parts by weight of elastomer (phr).

TABLE 1

|  | Composition 1 | Composition 2 |
|---|---|---|
| NR (1) | 100 | 100 |
| N220 (2) | 47.5 | 47.5 |
| Paraffin | 1 | 1 |
| TMQ (3) | 1 | 1 |
| 6-PPD (4) | 1.5 | 1.5 |
| Stearic acid | 2.5 | 2.5 |
| ZnO | 2.7 | 2.7 |
| Sulphur | 1.5 | 1.5 |
| Vulcanization accelerator | 0.6* | 0.51** |

*CBS ("Santocure CBS" from Flexsys)
**N-Cyclohexyl-S-(1,3,4-thiadiazol-2-yl)thiohydroxyl-amine
(1) Natural rubber
(2) Carbon black
(3) TMQ: 2,2,4-trimethyl-1,2-dihydroquinoline, sold by Flexsys
(4) Antioxidant 6-p-phenylenediamine

| | 1 | 2 | 3 | 4 | 5 | 6 | 7 | 8 | 9 | 10 |
|---|---|---|---|---|---|---|---|---|---|---|
| δ $^1$H (ppm) | 2.57 | — | — | 5.40 | 2.68 | 1.84 1.11 | 1.60 1.16 | 1.46 1.06 | 1.60 1.16 | 1.84 1.11 |

The rubber composition 2 comprising N-cyclohexyl-S-(1,3,4-thiadiazol-2-yl)thiohydroxylamine is identical to composition 1, it being understood that the CBS is replaced with an isomolar amount of N-cyclohexyl-S-(1,3,4-thiadiazol-2-yl)thiohydroxylamine.

The rheometric properties at 150° C. are given in Table 2.

TABLE 2

|  | Composition 1 (CBS) | Composition 2 (Compound B) |
|---|---|---|
| Rheo. prop. (DIN) | 150° C. | |
| Δtorque (dN · m) | 7.0 | 6.3 |
| k (min$^{-1}$) | 0.323 | 0.208 |
| $t_0$ (min) | 4.9 | 3.2 |
| $t_{99}$ (min) | 19.2 | 25.3 |

The rheometric properties obtained for the composition comprising N-cyclohexyl-S-(1,3,4-thiadiazol-2-yl)thiohydroxylamine are equivalent to those obtained for the composition comprising CBS. It is thus noted that the use of N-cyclohexyl-S-(1,3,4-thiadiazol-2-yl)thiohydroxylamine as accelerator for a tire rubber composition makes it possible to obtain a compromise with regard to the various rheometric properties similar to that obtained with vulcanization accelerators conventionally used for this application.

It is furthermore noted that compound B, and the compounds of formula (I) in general, advantageously replace, with regard to the environmental impact, sulphenamides comprising a mercaptobenzothiazole ring system, by not generating, in contrast to the latter, mercaptobenzothiazole on decomposing during the curing.

The invention claimed is:

1. A thiadiazole of formula (I):

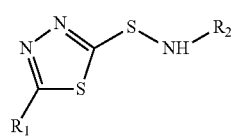

(I)

where
$R_1$ represents H or a $C_1$-$C_{25}$ hydrocarbon group chosen from linear, branched or cyclic alkyl groups and aryl groups which are optionally interrupted by one or more heteroatoms,
$R_2$ represents:
a cyclic $C_3$-$C_{10}$ alkyl group which is optionally interrupted by one or more heteroatoms and which is optionally substituted by one or more linear, branched or cyclic $C_1$-$C_{25}$ alkyl or $C_6$-$C_{12}$ aryl groups which are optionally interrupted by one or more heteroatoms.

2. The thiadiazole according to claim 1, wherein $R_1$ represents H.

3. The thiadiazole according to claim 2, wherein $R_1$ represents a methyl group.

4. The thiadiazole according to claim 1, wherein $R_2$ represents a cyclohexyl group.

5. A process for the preparation of a thiadiazole as defined in claim 1, comprising the steps of:
the starting compound is compound (A) of following formula:

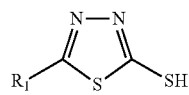

(A)

where $R_1$ is as defined in claim 1,
compound (A) is reacted with a compound of formula $R_2NH_2$, where $R_2$ is as defined in claim 1, in the presence of a base, then
an oxidizing composition comprising at least one oxidizing agent is added to the reaction medium, in order to obtain the thiadiazole of formula (I).

6. The process according to claim 5, wherein the base is sodium hydroxide.

7. The process according to claim 5, wherein the oxidizing agent is selected from the group consisting of iodine and sodium hypochlorite.

8. A process comprising a step of incorporating as a vulcanization accelerator, a thiadiazole of formula (I) as defined below, into a rubber composition for the manufacture of tires, based on one or more diene elastomers, on one or more reinforcing fillers, and on a vulcanization system:

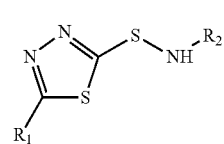

(I)

where
$R_1$ represents H or a $C_1$-$C_{25}$ hydrocarbon group selected from linear, branched or cyclic alkyl groups and aryl groups which are optionally interrupted by one or more heteroatoms,
$R_2$ represents:
a linear $C_2$-$C_{25}$ or branched $C_3$ or $C_5$-$C_{25}$ alkyl group which is optionally interrupted by one or more heteroatoms and which is optionally substituted by one or more cyclic $C_3$-$C_{10}$ alkyl or $C_6$-$C_{12}$ aryl groups, or
a cyclic $C_3$-$C_{10}$ alkyl group which is optionally interrupted by one or more heteroatoms and which is optionally substituted by one or more linear, branched or cyclic $C_1$-$C_{25}$ alkyl or $C_6$-$C_{12}$ aryl groups which are optionally interrupted by one or more heteroatoms.

9. The process according to claim 5, wherein the oxidizing composition is an aqueous sodium hypochlorite solution.

10. A thiadiazole of formula (I):

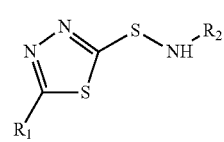

(I)

where
$R_1$ represents H,
$R_2$ represents:
a linear $C_2$-$C_{25}$ or branched $C_3$ or $C_5$-$C_{25}$ alkyl group which is optionally interrupted by one or more heteroatoms and which is optionally substituted by one or more cyclic $C_3$-$C_{10}$ alkyl or $C_6$-$C_{12}$ aryl groups, or a cyclic $C_3$-$C_{10}$ alkyl group which is optionally interrupted by one or more heteroatoms and which is optionally substituted by one or more linear, branched or cyclic $C_1$-$C_{25}$ alkyl or $C_6$-$C_{12}$ aryl groups which are optionally interrupted by one or more heteroatoms.

* * * * *